United States Patent [19]

Williams

[11] Plant 4,138

[45] Nov. 1, 1977

[54] ROSE PLANT

[76] Inventor: J. Benjamin Williams, 2800 Elnora St., Silver Spring, Md. 20902

[21] Appl. No.: 734,453

[22] Filed: Oct. 21, 1976

[51] Int. Cl.[2] ..... A01H 5/00

[52] U.S. Cl. ..... Plt./17

[58] Field of Search ..... Plt./17

*Primary Examiner*—Robert E. Bagwill

*Attorney, Agent, or Firm*—Vincent G. Gioia

[57] ABSTRACT

This invention relates to a winter-hardy grandiflora rose variety having long-lasting, iridescent, orange-red blossoms.

1 Drawing Figure

The present invention relates to a new and distinct variety of rose plant of the grandiflora rose class, which was originated by my crossing as seed parent the rose variety known as "Queen Elizabeth" and the rose variety known as "Comanche".

Among the novel characteristics possessed by this new variety which distinguish it from its parents and all other varieties of which I am aware are: (1) brilliant iridescent orange-red coloring of the inner petal surfaces, (2) long lasting blooms holding their color well on the plant and after cutting, having petals that drop off cleanly on aging, and (3) a vigorous plant which is "winter hardy" and produces flowers borne singly and several together as sprays. Asexual reproduction by budding of the new variety as performed in Chester County, Pa., shows that the foregoing and other distinguishing characteristics come true to form and are established and transmitted through succeeding propagations.

The new and improved rose variety which I have developed is an unusually vigorous upright growing grandiflora rose with unusual brilliant orange-red coloring of iridescent quality. The flowers have excellent bud form and open well in varied weather conditions. The color of the blooms holds well and the appearance is not adversely affected by rain or heat. A strong fresh tea fragrance compliments the beauty of the flowers.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—"Queen Elizabeth".

*Pollen parent.*—"Comanche".

Class: Grandiflora.

The following observations are made of specimens grown in Chester County, Pennsylvania during the month of June.

FLOWER

Blooming habit: Continuous.

Bud:

*Size.*—Medium.

*Form.*—Pointed.

*Color.*—When sepals first divide — 43A. When petals begin to unfurl — 40A. When half-blown: inside of petals — 40B; reverse side of petals — 43B.

*Sepals.*—Medium, tapered, curling back as bud opens extending $\frac{1}{3}$–$\frac{1}{2}$ the length of the open bud.

*Sepals color.*—Inside — 148C; outside — near 143C.

*Peduncle.*—Length — $2\frac{1}{2}$ to 3 inches. Strength — erect. Color — near 143C. Aspect — Smooth.

Bloom:

*Size.*—Average size when fully expanded — 4 to $4\frac{1}{2}$ inches.

*Borne.*—Singly and several together in sprays of 3 to 5 blooms.

*Form.*—High centered; petals remaining at first loosely rolled outward becoming ruffled at maturity; excellent bud form and to $\frac{3}{4}$ open, flower holds well.

*Petalage.*—Number of petals under normal conditions — 36.

*Color (during first two days).*—Inner petals at center of flower—40A. Outer petals—near 41B. Base of petals (point of attachment)—33A. Reverse of petals—41B. General tonality from a distance—near 40B.

*Color change.*—As bloom ages — center of inner petal takes on an iridescent orange-red cast (33A) color holds well cut or on bush. General tonality 3 or more days — 33A to 33B.

Petals:

*Texture.*—Thick.

*Appearance.*—Inside — velvety; Outside — satiny. Slight veining at base, not effected by rain or heat.

*Form.*—Rounded, slight notching.

*Arrangement.*—Imbricated, regularly arranged shingle-like.

*Petaloids in center.*—Few, small.

*Persistence.*—Drop off cleanly.

*Fragrance.*—Strong fresh tea.

*Lasting quality.*—Very good on plant and as cut flower and hold their brilliant color.

REPRODUCTIVE ORGANS

Stamens, filaments and anthers:

*Arrangement.*—Medium size, regularly arranged around styles.

*Color.*—22B.

Pollen: Color — 22A.

Styles: Bunched, uneven, short, thin.

Stigmas: Color — pink with cream tips.

Hips:

*Shape.*—Globular.

*Size.*—Medium.

*Color.*—169 C.

*Do seeds protrude.*—Slight.

PLANT

Form: Upright compact.

Growth: Very vigorous, uniform branching on main stems, new growth occurs regularly through season. Height attained — 3½ to 4 ft. in first season.

Foliage: Compounded 3 to 5 leaflets on single bloom, 5 to 7 leaflets on main canes.

*Size.*—Medium to large.

*Quantity.*—Abundant, cover plant to ground.

*Color.*—New foliage: Upper side — near to 183A with deep green veining. Under side — greenish red with 183C overcast. Old Foliage: Upper side — holly green, somewhat near but darker than 137B. Under side — 137C.

*Shape.*—Oval, pointed.

*Texture.*—Upper side — leathery, glossy. Under side — smooth between ribs.

*Edge.*—Serrated.

*Serration.*—Very small and uniform.

*Leaf stem.*—Color — 137B. Under side — 137C.

*Stipules.*—Medium smooth.

*Resistance to disease.*—Blackspot — highly resistant. Mildew — highly resistant.

Wood:

*New wood.*—Color — 137C. Bark — smooth.

*Old wood.*—Color — 137B. Bark — smooth.

Thorns:

*Thorns.*—Quantity — ordinary. On laterals from stalk — few. Form — flat base. Length — small. Color (when young) — 148C. Position — irregular.

*Prickles.*—Quantity — few. On laterals — very few.

Winter hardiness: Good winter hardiness, no protection needed.

I claim:

1. A new and distinct variety of rose plant of the grandiflora class, substantially as shown and described, characterized particularly by recurrent flowers borne singly and in sprays of 3 to 5 blooms having brilliant orange-red cast at the inner petals with iridescent quality on an upright compact plant of above average winter hardiness and disease resistance.

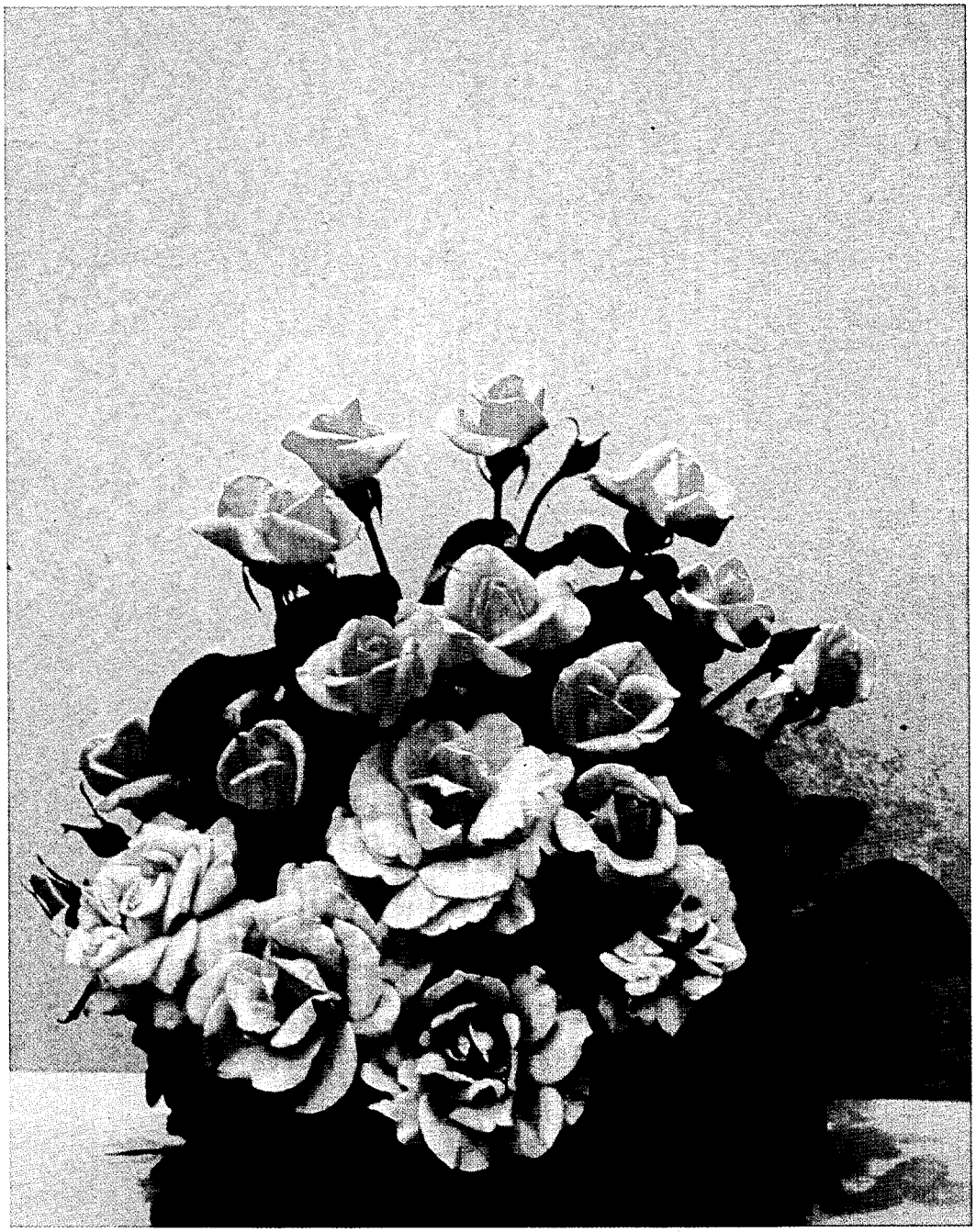

* * * * *